United States Patent
Wieczorek et al.

(10) Patent No.: US 10,942,282 B2
(45) Date of Patent: Mar. 9, 2021

(54) COMBINED IMAGING DETECTOR FOR X-RAY AND NUCLEAR IMAGING

(71) Applicant: KONINKLIJKE PHILIPS N.V., Eindhoven (NL)

(72) Inventors: Herfried Karl Wieczorek, Aachen (DE); Johannes Wilhelmus Maria Jacobs, Boxtel (NL); Herman Stegehuis, Best (NL); Alessandro Radaelli, Oirschot (NL); Christiaan Kok, Eindhoven (NL); Peter Lex Alving, Mierlo (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/329,824

(22) PCT Filed: Sep. 6, 2017

(86) PCT No.: PCT/EP2017/072277
§ 371 (c)(1),
(2) Date: Mar. 1, 2019

(87) PCT Pub. No.: WO2018/050496
PCT Pub. Date: Mar. 22, 2018

(65) Prior Publication Data
US 2019/0243005 A1 Aug. 8, 2019

(30) Foreign Application Priority Data
Sep. 13, 2016 (EP) ...................................... 16188564

(51) Int. Cl.
*G01T 1/20* (2006.01)
*G01T 1/164* (2006.01)
(Continued)

(52) U.S. Cl.
CPC ............ *G01T 1/1644* (2013.01); *A61B 6/037* (2013.01); *A61B 6/06* (2013.01); *A61B 6/4233* (2013.01);
(Continued)

(58) Field of Classification Search
CPC ... G01T 1/1644; G01T 1/1611; G01T 1/1647; G01T 1/1648; A61B 6/486;
(Continued)

(56) References Cited

U.S. PATENT DOCUMENTS 6,362,480 B1 3/2002 Peter
6,366,643 B1 * 4/2002 Davis et al.
(Continued)

FOREIGN PATENT DOCUMENTS

NL 1030168 4/2007
WO 2007/105942 9/2007
(Continued)

OTHER PUBLICATIONS

Beijst, et al.: "A Parallel-Cone Collimator for High-Energy SPECT", The Journal of Nuclear Medicine, vol. 56, No. 3, Mar. 2015.

*Primary Examiner* — Kiho Kim

(57) ABSTRACT

The invention relates to a combined imaging detector for detection of gamma and x-ray quanta comprising an x-ray detector (31) for generating x-ray detection signals in response to detected x-ray quanta and a gamma detector (32) for generating gamma detection signals in response to detected gamma quanta. The x-ray detector (31) and the gamma detector (32) are arranged in a stacked configuration along a radiation-receiving direction (33). The gamma detector (32) comprises a gamma collimator plate (320) comprising a plurality of pinholes (321), and a gamma conversion layer (322, 324) for converting detected gamma quanta into gamma detection signals.

23 Claims, 4 Drawing Sheets

(51) Int. Cl.
  *A61B 6/00* (2006.01)
  *A61B 6/03* (2006.01)
  *G01T 1/161* (2006.01)
  *A61B 6/06* (2006.01)

(52) U.S. Cl.
  CPC .......... *A61B 6/4258* (2013.01); *A61B 6/4291* (2013.01); *A61B 6/4417* (2013.01); *A61B 6/4441* (2013.01); *A61B 6/486* (2013.01); *A61B 6/487* (2013.01); *A61B 6/5235* (2013.01); *G01T 1/1611* (2013.01); *G01T 1/1647* (2013.01); *G01T 1/1648* (2013.01)

(58) Field of Classification Search
  CPC ..... A61B 6/4441; A61B 6/4233; A61B 6/487; A61B 6/037; A61B 6/4417; A61B 6/5235; A61B 6/4291; A61B 6/06; A61B 6/4258

See application file for complete search history.

(56) References Cited

U.S. PATENT DOCUMENTS

| | | | |
|---|---|---|---|
| 6,392,235 B1* | 5/2002 | Barrett | G01T 1/295 250/363.06 |
| 6,448,559 B1 | 9/2002 | Saoudi | |
| 9,261,611 B2* | 2/2016 | Shahar | G01T 1/1648 |
| 9,431,140 B2* | 8/2016 | Mok | G01T 1/1648 |
| 9,907,518 B2* | 3/2018 | Gooβen | A61B 6/0492 |
| 2006/0000978 A1* | 1/2006 | Engdahl | G01T 1/1648 250/363.1 |
| 2008/0001088 A1* | 1/2008 | Joung | G01T 1/1644 250/363.1 |
| 2012/0061581 A1 | 3/2012 | Hugg | |
| 2012/0265050 A1 | 10/2012 | Wang | |
| 2013/0126744 A1* | 5/2013 | Jansen | H01L 31/085 250/370.08 |
| 2015/0320375 A1* | 11/2015 | De Jong | A61B 6/4258 378/63 |

FOREIGN PATENT DOCUMENTS

| | | |
|---|---|---|
| WO | 2009/047328 | 4/2009 |
| WO | 2010/014001 | 2/2010 |

* cited by examiner

COMBINED IMAGING DETECTOR FOR X-RAY AND NUCLEAR IMAGING

CROSS REFERENCE TO RELATED APPLICATIONS

This application is the U.S. National Phase application under 35 U.S.C. § 371 of International Application No. PCT/EP2017/072277 filed Sep. 6, 2017, published as WO 2018/050496 on Mar. 22, 2018, which claims the benefit of European Patent Application Number 16188564.5 filed Sep. 13, 2016. These applications are hereby incorporated by reference herein.

FIELD OF THE INVENTION

The invention relates to a combined imaging detector for detection of gamma and x-ray quanta and to a corresponding imaging system. It finds application in the medical field, more particularly in the fields of medical imaging and medical interventions, and may be used for example to provide an x-ray image and a corresponding nuclear image of a region of interest. A gamma detector is also disclosed.

BACKGROUND OF THE INVENTION

In various medical imaging procedures it is beneficial to provide both an x-ray image and a nuclear image of a region of interest. The x-ray image typically provides structural information indicative of the anatomy of the region of interest. The nuclear image, defined herein to mean an image indicative of radiotracer distribution in an object, is generated based on detected gamma quanta. The nuclear image may for example be a gamma scintigraphy or a SPECT image and typically provides functional, or physiological information relating to the region of interest. Together the two different image types can be used to improve the identification of an underlying pathology during a medical investigation.

Various medical procedures also benefit from a combination of x-ray and nuclear imaging. Selective internal radiation therapy, or SIRT, is one such medical procedure in which radiation is used to treat cancer. SIRT is often used for non-resectable cancers, i.e. cancers that cannot be treated surgically, and involves injecting microspheres of radioactive material into the arteries that supply the tumor. Liver tumours or metastases are often treated in this way. However, in delivering such therapy, a number of workflow steps are required in order to prevent potential side effects. These steps may include the closure of atypical lung and gastrointestinal shunts before injection of Yttrium-90-containing microspheres. This prevents radiation ulcers which might otherwise be triggered by extra-hepatic localization of administered micro-spheres. For this purpose, catheter-based vessel coiling is performed under x-ray guidance during a minimally-invasive procedure. Afterwards, the remaining shunt level towards lungs and gastrointestinal area may be controlled by injection of Technetium $^{99m}$Tc albumin aggregated, i.e. Tc-labeled MAA, into both main liver arteries followed by planar gamma imaging. During this procedure the patient is typically repeatedly transported between a cath lab and SPECT imaging room.

Further, in oncological interventions x-ray is used, mostly using a fixed C-arm. For treatment planning or follow-up during interventions, tomographic imaging methods like CT, SPECT or PET are used. Especially the change between intervention (under C-arm control) and follow-up (e.g. by SPECT) is inadequate for the clinical workflow since the patient must be transported into another imaging system or another room and undergo multiple sessions including a liver-to-lung shunting evaluation (work-up) and then the actual therapy delivery.

U.S. Pat. No. 6,448,559 B1 discloses a detector assembly for multi-modality PET/SPECT/CT scanners. The detector assembly comprises a first layer for detecting low energy gamma radiation and x-rays and a second layer for detecting high energy gamma radiation. The first layer is generally transparent to high energy gamma radiation. The detector assembly includes a photodetector in the form of an avalanche photodiode to transform the light signals from the scintillators into electric signals. The detector assembly may be incorporated in a multi-modality PET/SPECT/CT scanner for simultaneous transmission and emission imaging with the same detection geometry. In one example configuration a collimator is positioned in front of the detector assembly to define preferential incidence directions for SPECT photons.

However, in the field of medical imaging, and in the field of medical procedures, there remains a need for improved imaging systems that are capable of providing both a nuclear image and an x-ray image.

SUMMARY OF THE INVENTION

It is an object of the invention to provide a combined imaging detector for detection of gamma and x-ray quanta and a corresponding imaging system that are capable of providing both a nuclear image and an x-ray image of a region of interest. Another object of the invention is to provide an improved gamma detector.

According to one aspect of the present invention a combined imaging detector is presented for detection of gamma and x-ray quanta, said combined imaging detector comprising:

an x-ray detector for generating x-ray detection signals in response to detected x-ray quanta; and a gamma detector for generating gamma detection signals in response to detected gamma quanta, said x-ray detector and said gamma detector being arranged in a stacked configuration along a radiation-receiving direction, wherein said gamma detector comprises a gamma collimator plate comprising a plurality of pinholes; and a gamma conversion layer for converting detected gamma quanta into gamma detection signals.

According to another aspect of the present invention an imaging system is presented comprising:

an x-ray source for emitting pulsed x-ray radiation, and a combined imaging detector as disclosed herein for detection of gamma and x-ray quanta.

Preferred embodiments of the invention are defined in the dependent claims. It shall be understood that the claimed imaging system has similar and/or identical preferred embodiments as the claimed detector, in particular as defined in the dependent claims and as disclosed herein.

The present invention is based on the idea to combine an x-ray detector with a gamma detector (also called a gamma-ray detector), in particular comprising an array of gamma photodetector elements, positioned just behind the x-ray detector (seen in the direction of radiation from its source to the detector). The gamma detector uses a common gamma collimator plate (also called gamma-ray collimator plate) with multiple pinholes for respective gamma photodetector elements. Simultaneous or subsequent or consecutive x-ray and gamma images can be taken by use of a pulsed x-ray radiation (e.g. using 15 ms or shorter x-ray pulses) and intermittent capture of gamma quanta on the gamma detector. For example within a frame period of e.g. 40-250 ms there would be 25-235 ms available for gamma capture when the x-ray radiation is switched off. A longer frame period than 250 ms may clearly also be used, e.g. 500 ms or 1000 ms or longer. This may be advantageous for example when less regular x-ray images are desired, for example in order to reduce the x-ray dose.

In this way a much better way of image guided intervention can be achieved by the simultaneous use of both anatomical imaging (e.g. x-ray or CT) and molecular imaging (e.g. gamma imaging or SPECT). An x-ray and gamma image for the whole region of interest can be acquired in the body simultaneously, including tomographic images. This solution can also be applied advantageously to guide surgical oncology procedures (e.g. lung, thyroid, and so forth) currently performed with the use of gamma probes with small field-of-view (and disconnected from x-ray imaging) and to enable percutaneous x-ray guided interventions (e.g. tumor ablation and biopsy) to track tumor location during needle/antenna insertion.

In the context of the present invention, x-ray quanta and gamma quanta can be detected simultaneously, quasi-simultaneously or consecutively or subsequently (e.g. alternately). The time spacing between the detection of x-ray quanta and gamma quanta can be much reduced in comparison to the current workflow using known detectors. Simultaneous detection is e.g. possible by measuring gamma quanta during the time period when x-ray imaging is performed e.g. in case of low-energy x-rays.

The x-ray detector as well as the gamma detector may generally be formed as direct detector or an indirect detector, i.e. four general combinations are possible (direct x-ray detector+direct gamma detector; direct x-ray detector+indirect gamma detector; indirect x-ray detector+direct gamma detector; indirect x-ray detector+indirect gamma detector).

Thus, in an embodiment said gamma conversion layer (also called gamma-ray conversion layer) includes a direct gamma conversion layer or an indirect gamma conversion layer. The direct gamma conversion layer preferably comprises a combination of a gamma photoconductor layer comprising a plurality of photoconductor elements for generating gamma detection signals in response to detected gamma quanta and a gamma sensor array for sensing said gamma detection signals. The indirect conversion layer preferably comprises a gamma scintillator layer comprising a plurality of gamma scintillator elements for generating gamma scintillation light signals in response to detected gamma quanta and a gamma photodetector array for converting said gamma scintillation light signals into gamma detection signals.

According to a preferred embodiment the gamma detector is controlled to generate gamma detection signals when no x-ray quanta are incident on the combined imaging detector. Particularly during intervals between x-ray pulses in case of pulsed x-ray emission the gamma detector detects gamma quanta and generates gamma detection signals. In certain applications x-ray radiation may not be used, in which case only nuclear images may be taken. This could also be alternated, e.g. for a few seconds an x-ray detection signals may be acquired and then for a few minutes gamma detection signals may be acquired.

Preferably, the number of pinholes of said gamma collimator plate is equal to or smaller than the number of gamma detector elements of the gamma conversion layer, wherein one pinhole and one or more corresponding gamma detector elements are arranged in a stacked configuration along the radiation-receiving direction and the pinhole is centered with respect to the one or more corresponding gamma scintillator elements. Thus, in one embodiment a one-to-one configuration is given between pinholes and gamma detector elements, wherein the pinhole is centered above the gamma detector element. In another embodiment a one-to-multiple configuration is given between pinholes and gamma detector elements, wherein one pinhole is centered above a group of gamma detector elements, which enables an increased resolution of the nuclear image. Hereby, in an indirect gamma detector, one gamma scintillator element (also called gamma scintillator crystal) is generally associated with one gamma photodetector element of a gamma photodetector array. Thus, the one or more gamma scintillator elements and the associated one or more gamma photodetector elements may together be regarded as gamma photodetector module (which may also be seen as a detector module structured into one or more gamma-sensitive pixels), which is associated with a pinhole.

The gamma collimator plate may e.g. be made from a lead or tungsten plate, in which the plurality of pinholes are formed. Alternatively, the gamma collimator plate may be made from an absorption plate, in which a plurality of pinhole inserts, e.g. made from tungsten or gold, including said pinholes are integrated, wherein the absorption plate can be less exactly built.

The pinholes are preferably knife-edge or tapered pinholes, wherein each pinhole has a projection area on the respective one or more associated gamma scintillator element(s).

In an embodiment the x-ray detector comprises an x-ray conversion layer for converting detected x-ray quanta into x-ray detection signals, said x-ray conversion layer including either a direct x-ray conversion layer or an indirect x-ray conversion layer. The direct x-ray conversion layer preferably comprises a combination of an x-ray photoconductor layer comprising a plurality of photoconductor elements for generating x-ray detection signals in response to detected x-ray quanta and an x-ray sensor array for sensing said x-ray detection signals. The indirect x-ray conversion layer comprises a combination of an x-ray scintillator layer comprising a plurality of x-ray scintillator elements for generating x-ray scintillation light signals in response to detected x-ray quanta and an x-ray photodetector array for converting said x-ray scintillation light signals into x-ray detection signals. In this embodiment the x-ray detector may further include an x-ray anti-scatter grid.

Preferably the x-ray detector is a so-called "detector-on-foil" that is formed on a foil (for example a polymer foil) and which includes read-out electronics that are arranged laterally with respect to the x-ray conversion layer (e.g. of the x-ray scintillator layer) and/or the x-ray anti-scatter grid. This arrangement increases the transmission rate for gamma quanta through the x-ray detector.

In another embodiment the material of the x-ray conversion layer (e.g. the scintillator layer and/or the x-ray photodetector array) adjacent to a pinhole is removed or thinner than in other areas not adjacent to a pinhole, which further increases the transmission rate of gamma quanta through the pinholes.

In preferred embodiments the plurality of pinholes each have a projection area having a round, square, or hexagonal shape. Generally, other projections areas are possible as well. The desired projection area depends e.g. on the manufacturing process and on the desired efficiency of use of the complete projection area of all pinholes.

In one embodiment the projection areas of neighboring pinholes overlap, whereas in another embodiment the projection areas of neighboring pinholes are separated by septa. Overlap increases system sensitivity, but should be limited so that reconstruction of the obtained detection signals does not get too difficult or complex. Detection signals obtained by an imaging detector having non-overlapping projections areas of pinholes are easier to reconstruct, but such pinholes result in less system sensitivity.

The imaging system may further, in addition to the x-ray source and the combined imaging detector, comprise a control unit for controlling said combined imaging detector to detect gamma quanta during intervals between x-ray pulses. The control unit may additionally control the x-ray source to control the length and periodicity of the x-ray pulses. Moreover, the control unit may either i) identify gamma detection signals generated during x-ray pulses or ii) control said combined imaging detector to inhibit or suppress the generation of gamma detection signals during said x-ray pulses. By so identifying or inhibiting the generation of gamma detection signals, such signals may be excluded from reconstruction of a corresponding gamma image. Since the absorption of x-ray quanta in the x-ray detector is a probabilistic process, a small proportion of x-ray quanta may pass through the x-ray detector and be detected by the gamma detector. Therefore by excluding these gamma detection signals from reconstruction of a corresponding gamma image, interference between the x-ray detection signals and the gamma detection signals may be reduced. Preferably the control unit is configured to control the combined imaging detector to generate gamma detection signals only during intervals between x-ray pulses.

According to an embodiment the x-ray source is configured to emit two split x-ray beams at different angles. Hereby, a small angle in the range of less than or equal to 10° or less than or equal to 5° may be sufficient. This may reduce the potential effect of small missing X-ray image areas on image quality e.g. in pulsed fluoroscopy.

According to another aspect a gamma detector for generating gamma detection signals in response to detected gamma quanta is provided. The gamma detector includes: a gamma collimator plate comprising a plurality of pinholes; a gamma conversion layer for converting detected gamma quanta into gamma detection signals; and an actuator. The gamma collimator plate and the gamma conversion layer are arranged in a stacked configuration along a radiation-receiving direction. The actuator is configured to provide either i) a relative displacement between the gamma collimator plate and the gamma conversion layer, or ii) a displacement of the gamma detector, in a displacement direction that is perpendicular to the radiation-receiving direction. In so doing, sufficient gamma detection signals may be generated by the gamma detector to reconstruct a tomographic, i.e. SPECT gamma image. The gamma detector may be included within the above-described combined imaging detector. Advantageously the gamma detector, i.e. a single gamma camera, may be used to provide tomographic data.

DETAILED DESCRIPTION OF THE INVENTION

Figure 1:
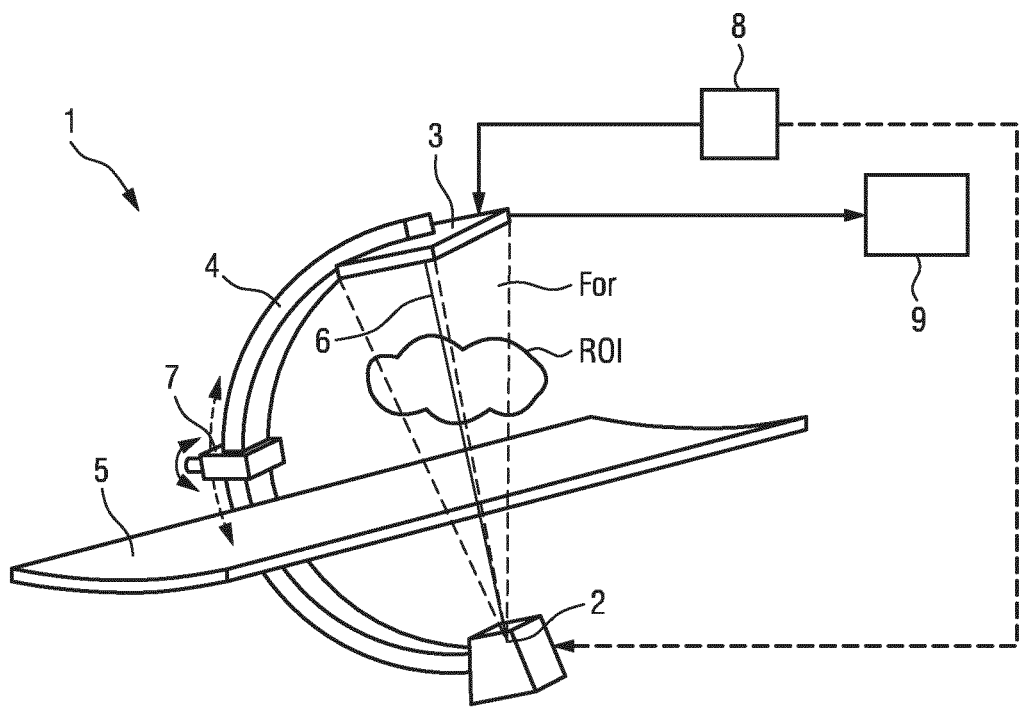
FIG. 1 illustrates an embodiment of an imaging system according to the present invention.

FIG. 1 illustrates an embodiment of an imaging system 1 according to the present invention. The imaging system 1 comprises an x-ray source 2, a combined imaging detector 3, a C-arm 4, and a patient table 5. The x-ray source 2 is attached to a first portion of C-arm 4 and the detector 3 is attached to a second portion of the C-arm 4. The x-ray source 2 and the detector 3 are so-positioned in order to measure x-ray transmission along path 6 between the x-ray source 2 and the detector 3. The field-of-view FOV of the x-ray source detector arrangement in FIG. 1 is illustrated by the short dashed lines that comprises path 6. The combined imaging detector 3 can be used for simultaneous (or subsequent or consecutive or alternate) detection of gamma and x-ray quanta to generate an x-ray image and a nuclear image for the same region of interest ROI.

The x-ray source 2 can be a standard x-ray source, although it is also contemplated to use a dual energy source in this position. Preferably, the x-ray source emits pulsed x-ray radiation so that gamma quanta in the intervals between x-ray pulses can be detected. The C-arm 4 may be a standard C-arm as commonly used in x-ray imaging and may be mounted in a fixed position or optionally arranged for various movements, e.g. as illustrated by the arrows near its support 7. Various modes of scanning are generally possible with such an imaging system.

Optionally, a control unit 8 is provided for controlling the detector 3 to detect gamma quanta during intervals between x-ray pulses. Control unit 8 may be used in combination with any of the embodiments illustrated in the Figures. Specifically the control unit may be operated in combination with x-ray detector 41 described with reference to FIG. 3 that includes a so-called detector-on-foil arrangement, or with x-ray detector 31 described with reference to FIG. 2. The control unit 8 may further control the x-ray source 2, in particular the pulse rate and pulse duration. Moreover, control unit 8 may either i) identify gamma detection signals generated by the gamma detector 32 during x-ray pulses for exclusion from a reconstruction of a corresponding gamma image or ii) control the gamma detector 32 to inhibit or suppress (i.e. reduce) the generation of gamma detection signals during said x-ray pulses. Both of these options may be used to remove, from a later reconstruction of a corresponding gamma image, the respective gamma detection signals. This may be achieved by for example monitoring the generated x-ray detection signals, or by monitoring a control signal that activates the x-ray source, and based on this signal, either tagging the gamma detection signals detected during the x-ray pulses, or gating, i.e. masking, the output of the x-ray detector in order to inhibit or suppress the signals. The gating may be performed electronically, for example by means of analogue or digital electronic switches that gate the outputs of the photoconductor elements of the gamma photoconductor layer. The tagging may be performed in software by for example setting a data field associated with temporal gamma detection signals that are contemporaneous with the x-ray pulses in order to identify the relevant gamma detection signals and has the advantage that no recovery times associated with electronically switching of the signals are experienced. By so identifying or inhibiting the generation of gamma detection signals, such signals may be excluded from reconstruction of a corresponding gamma image. Since the absorption of x-ray quanta in the x-ray detector is a probabilistic process, a small proportion of x-ray quanta may pass through the x-ray detector and be detected by the gamma detector. Therefore by excluding these gamma detection signals from reconstruction of a corresponding gamma image, interference between the x-ray detection signals and the gamma detection signals may be reduced. Moreover the control unit may be configured to control the gamma detector to generate gamma detection signals only during intervals between x-ray pulses. This may be achieved by for example monitoring the x-ray detection signals or x-ray source activation signals as described above and electronically disabling the generation of gamma detection signals during x-ray pulses, for example by either gating them or adjusting the power supplied to the gamma detector. Further, a processing unit 9, e.g. a workstation or computer, may be provided to process the acquired data, i.e. the x-ray detection signals and the gamma detection signals, for instance in order to reconstruct x-ray images and nuclear images.

Figure 2:
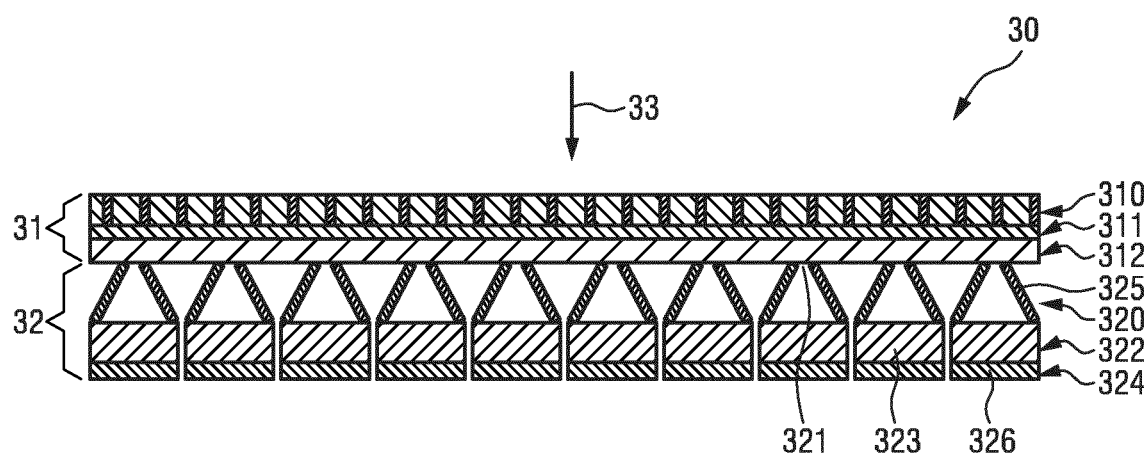
FIG. 2 illustrates a first embodiment of a combined imaging detector according to the present invention.

FIG. 2 illustrates a first embodiment of a combined imaging detector 30 according to the present invention. It comprises an x-ray detector 31 for generating x-ray detection signals in response to detected x-ray quanta and a gamma detector 32 for generating gamma detection signals in response to detected gamma quanta. The x-ray detector 31 and the gamma detector 32 are arranged in a stacked configuration along the radiation-receiving direction 33.

The gamma detector 32 comprises a gamma collimator plate 320 comprising a plurality of pinholes 321, a gamma scintillator layer 322 comprising a plurality of gamma scintillator elements 323 for generating gamma scintillation light signals in response to detected gamma quanta, and a gamma photodetector array 324 (preferably comprising a plurality of gamma photodetector elements 326) for converting said gamma scintillation light signals into gamma detection signals. In this embodiment the gamma collimator plate 320 is formed by a plurality of the pinhole cones 325 each having a small pinhole 321 facing the x-ray detector 31 and increasing in width towards the scintillator layer 322.

Thus, in this embodiment the gamma detector 32 is configured as indirect gamma detector comprising an indirect gamma conversion layer (formed by the gamma scintillator layer 322 and the gamma photodetector array 324). Instead, a direct gamma conversion detector may be used in which the indirect gamma conversion layer is replaced by a direct conversion layer comprising a combination of a gamma photoconductor layer comprising a plurality of photoconductor elements for generating gamma detection signals in response to detected gamma quanta and a gamma sensor array for sensing said gamma detection signals.

In FIG. 2 (and other figures) one gamma scintillator element 323 is arranged below one pinhole 321. It should be noted, however, that generally, a plurality (e.g. 8×8) gamma scintillator elements 323 will be arranged below (and thus correspond to) one pinhole 321.

While generally any kind of x-ray detector may be used as x-ray detector 31, in this embodiment of the combined imaging detector 30 the x-ray detector 31 is configured as indirect conversion x-ray detector comprising an x-ray anti-scatter grid 310, an x-ray scintillator layer 311 comprising a plurality of x-ray scintillator elements for generating x-ray scintillation light signals in response to detected x-ray quanta, and an x-ray photodetector array 312 (preferably comprising a plurality of x-ray photodetector elements) for converting said x-ray scintillation light signals into x-ray detection signals. Instead, a direct x-ray conversion detector may be used in which the indirect conversion layer (comprising the x-ray scintillator layer 311 and the x-ray photodetector array 312) is replaced by a direct x-ray conversion layer that directly converts x-ray quanta into electrical charges and preferably comprises an x-ray photoconductor layer comprising a plurality of photoconductor elements for generating x-ray detection signals in response to detected x-ray quanta and an x-ray sensor array for sensing said x-ray detection signals.

Using such a combined imaging detector has multiple advantages over known detectors such as:

The imaging field-of-view is centered on exactly the same region-of-interest for x-ray and gamma imaging. The gamma image may even be slightly larger than the x-ray imaging field.

Patient access for medical professionals is unchanged since the area of the composite detector is the same as a standard x-ray detector.

Simultaneous view at any angulation of the C-arm allowing hybrid 3D tomographic imaging (e.g. SPECT-CBCT)

No significant changes to the geometry and mechanics of the x-ray system thus enabling retro-fitting and upgrades of state-of-the-art C-arm systems.

Compared to a system using separate x-ray and gamma detectors there is no necessity of mechanical or electrical coupling of both detectors to ensure the same imaging FOV.

There is no danger of collision of different detectors.

Pinhole collimation is much better suited for high-energy gamma quanta than parallel-hole collimation since collimator scatter is strongly reduced.

Pinhole collimation using de-magnification results in a much higher gamma and SPECT sensitivity than conventional parallel-hole or related collimation (e.g. fan beam, cone beam).

Figure 3:
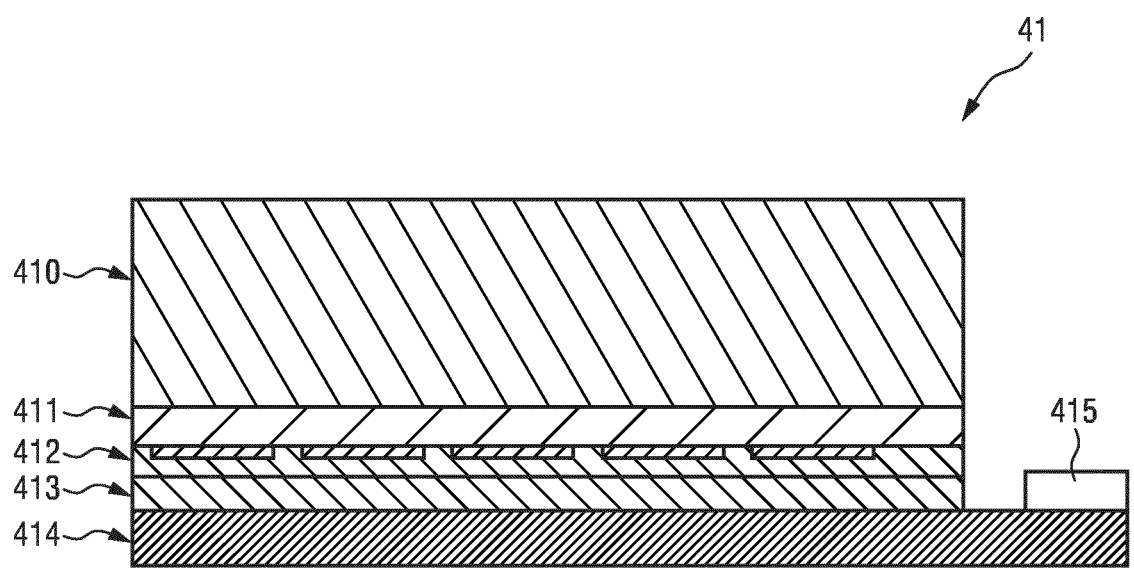
FIG. 3 illustrates an embodiment of an x-ray detector on foil usable in a combined imaging detector according to the present invention.

Another embodiment of an x-ray detector 41 that may be used in the combined imaging detector is illustrated in FIG. 3. The x-ray detector 41 may be built not on a (glass) plate, but as a detector-on-foil, with readout electronics 415 arranged laterally instead of the detector back-side. The x-ray detector 41 comprises a scintillator 410, an optical barrier and glue layer 411, a photodiode layer (e.g. <1 µm) 412, a thin film transistor (TFT)-backplane (e.g. <1-3 µm) 413, and a polymer foil (e.g. 10-50 µm) 414. Such an x-ray detector 41 may have 70% transmission for Tc-99m gamma quanta (140 keV), which is sufficient for a gamma detector arranged behind it in the radiation receiving direction.

While FIG. 3 shows an indirect x-ray detector, the lateral arrangement of the readout electronics is preferably also applied in case of a direct x-ray detector.

In an exemplary non-limiting implementation an x-ray detector on foil of 20×20 cm² size may be used. The gamma photodetector array may comprise 8×8 pixels in 32.6×32.6 mm² and a pixel size 4.0×4.0 mm². The gamma photodetector array may cover 6×6=36 arrays of a size of 196×196 mm². The gamma collimator may cover 6×6=36 tungsten pinhole arrays (having e.g. 3 mm openings).

A common multi-pinhole collimator (i.e. the collimator layer 320) can be built from a lead or tungsten plate with multiple pinholes centered in front of respective detector tiles. Alternatively, multiple pinhole inserts, e.g. made from tungsten or gold, can be placed in a less exactly built absorption plate. The use of a strongly absorbing plate avoids scatter of high-energy gamma quanta which typically gives a strong scatter background in parallel-hole collimation. The manufacturing and structure of pinholes for gamma imaging, e.g. knife-edge or tapered pinholes, is generally known. A typical pinhole plate thickness will be in the range 5-20 mm, preferably around 10 mm, depending on the material used.

Figure 4A:
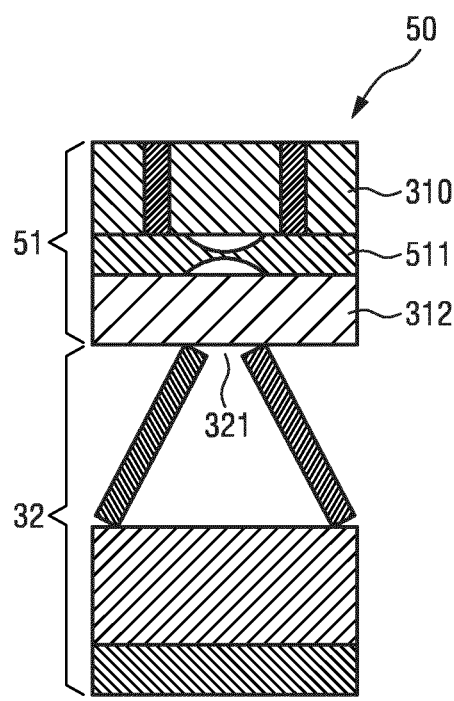
FIGS. 4A and 4B illustrate a second and a third embodiment of a combined imaging detector according to the present invention.
Figure 4B:
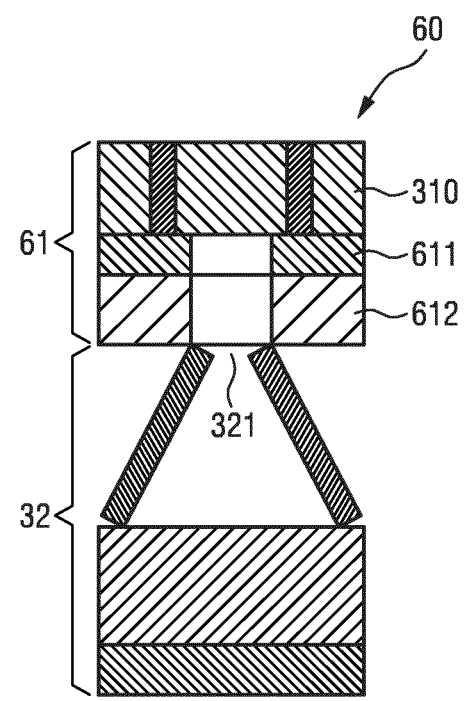

FIGS. 4A and 4B illustrate a second and a third embodiment of a combined imaging detector 50, 60 (partially and enlarged) according to the present invention. In the second embodiment of the detector 50 shown in FIG. 4A, the absorption of gamma rays in the x-ray detector 51, in front of the pinholes 321, is reduced to (almost) zero by local removal or thinning of the x-ray scintillator 511, e.g. by laser ablation of CsI in the x-ray detector 51. A similar effect is achieved by removal of x-ray scintillator 611 and x-ray sensor substrate 612 of the x-ray detector 61 on top of the pinholes 321 in the third embodiment of the detector 60 shown in FIG. 4B.

The resulting effect of small missing x-ray image areas on image quality in pulsed fluoroscopy can be minimized by splitting the x-ray beam in two angulated (twin) x-ray beams. This may not be required for 3D imaging, as small missing areas will not lead to visible image quality loss in 3D reconstruction, or software correction algorithms can be applied to correct any loss of data.

Figure 5:
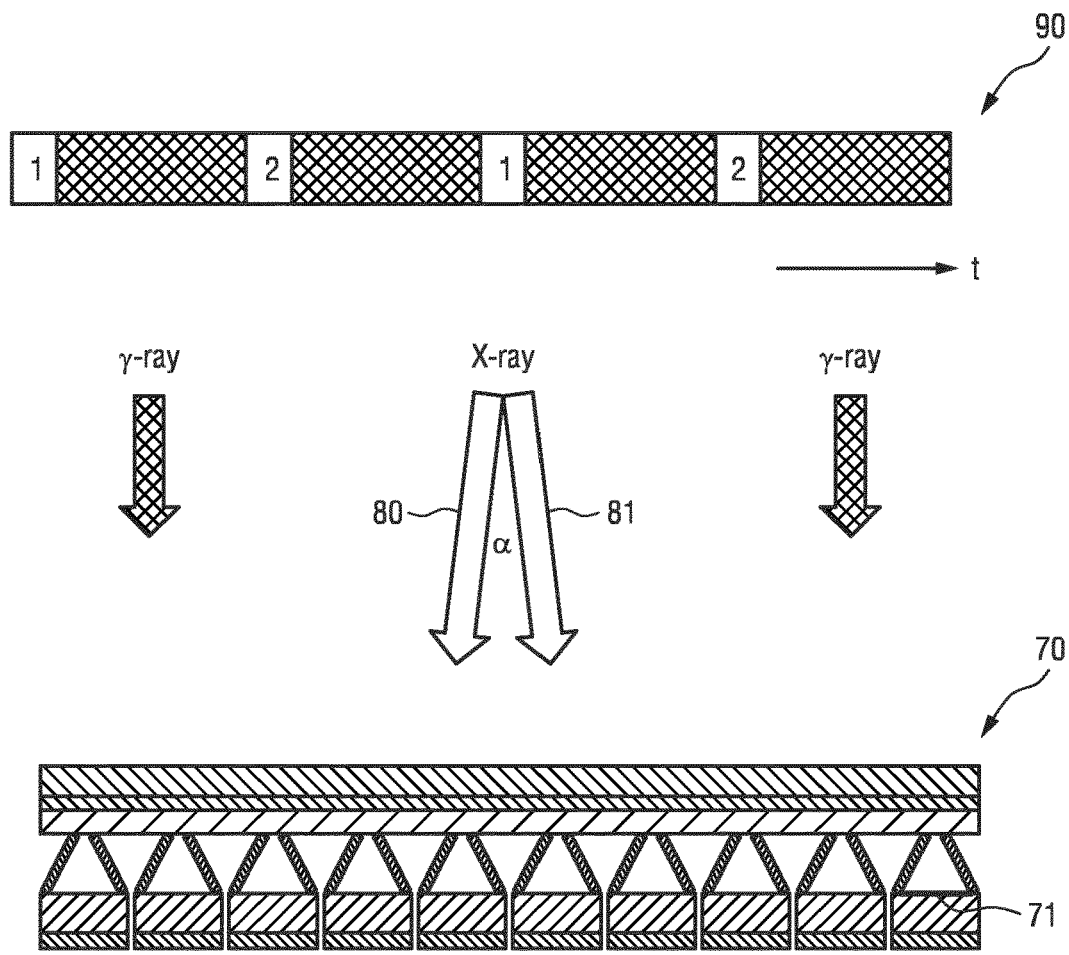
FIG. 5 illustrates a fourth embodiment of a combined imaging detector according to the present invention.

Assuming, as a non-limiting example, an object-pinhole distance of 200 mm, images from x-ray beams 1 and 2 are shifted horizontally 5 mm when $\alpha=1.4°$ ($=\tan^{-1}$ (5/200)). Hence, only a small angulation a is needed for pinholes with an exemplary diameter <5 mm. FIG. 5 illustrates a corresponding embodiment of a combined imaging detector 70 including a timing diagram 90 showing the alternate detection of x-ray quanta and gamma quanta. Here, the x-ray source is configured to emit two angulated x-ray beams 80, 81 as explained above. This may be achieved in several ways: by electron deflection in x-ray source, by two cathodes in the x-ray source, or by a sectioned rotating anode in the x-ray source.

De-magnification in pinhole imaging, i.e. the projection of a certain field-of-view through one pinhole onto a detector tile which is smaller in size than this field-of-view, allows use of multiple pinhole detectors with the same detector area as a conventional parallel-hole collimator, boosting, i.e. increasing SPECT system sensitivity without using larger detector area. This is possible with solid-state detectors that have high enough spatial resolution. A conventional Anger Camera is not suited because of its intrinsic spatial resolution. An exemplary geometry would be an object-pinhole distance of 10-20 cm and a pinhole-detector distance of 5 cm, so that the de-magnification factor would be 2-4, resulting in a 1.78 to 2.56 times higher sensitivity, compared to a non de-magnifying geometry, and overlapping images from a multitude of gamma radiation detectors. With this geometry and e.g. a pinhole diameter of 2 mm, spatial resolution in the object plane at 10-20 cm distance would be 6 and 10 mm, respectively. Pinhole diameters in the range of 1-5 mm may be preferred when optimizing for high spatial resolution or high sensitivity, respectively.

The gamma radiation detector as used in the proposed combined imaging detector may be built from an array of tiles of counting detectors in solid-state technology. Different technologies are available, either direct conversion detectors (typically built from cadmium-zinc telluride, CZT, or cadmium telluride, CdTe), or indirect detectors using a scintillator array in front of a silicon photomultiplier array (SiPM). A digital photon detector can be switched off during phases of x-ray illumination so that x-ray and gamma images can be obtained sequentially with a frame rate of e.g. up to 25 frames per second.

Figures 6A, 6B:
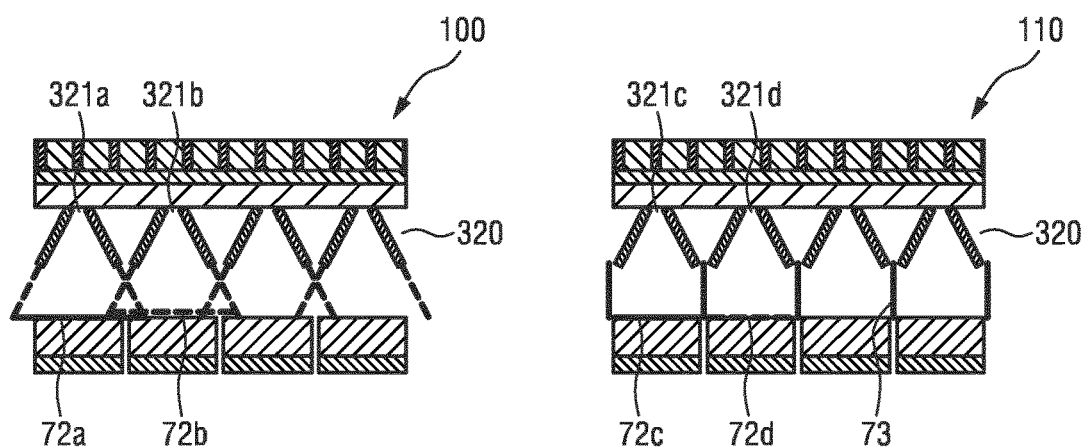
FIGS. 6A and 6B illustrate a fifth and a sixth embodiment of a combined imaging detector according to the present invention.

A typical arrangement of detector tiles behind a 20×20 cm² x-ray detector would be an array of 6×6 digital photon detector tiles (32.6 mm×32.6 mm each, 4 mm pixels), or a 10×10 array of CZT tiles (20×20 mm each, 2.46 mm pixels). The projection area 71 (see FIG. 5), i.e. the projection of the pinhole on the upper surface of the gamma scintillator layer of single pinholes can be round, in a square or hexagonal arrangement. The projection areas 72a, 72b may have limited overlap for different (neighboring) pinholes 321 (as illustrated in FIG. 6A showing another embodiment of a combined imaging detector 100). Alternatively, the projection areas 72c, 72d of different (neighboring) pinholes 321c, 321d may be separated from each other by extra septa 73 (as illustrated in FIG. 6B showing another embodiment of a combined imaging detector 110).

Possible scintillator materials for indirect gamma detection are NaI:Tl, CsI:Tl, cerium doped garnets like yttrium-aluminium garnets (YAG), gadolinium-aluminium garnets (GAG), gadolinium-gallium-aluminium garnets (GGAG), combinations thereof or with other rare earth materials like lutetium or terbium, cerium bromide $CeBr_3$, or praseodymium doped gadolinium oxisulfide (GOS). Other materials may be used as well.

The pixels on the gamma radiation detector tile may have a size of 4×4 mm. Higher spatial resolution is obtained when arrays of scintillator sticks of smaller dimensions are optically coupled to the gamma radiation detector. The position of the crystal in which a gamma quantum had been detected is obtained from a flood map measured on the detector. This principle has been proven for pre-clinical PET imaging with a pixel pitch of 1.2 mm and works for SPECT as well. In an embodiment arrays of ceramic garnet scintillators, arranged either from single ceramic scintillator sticks or produced in advanced manufacturing technologies, e.g. a tape-casting, injection moulding or green-body or brown-body ceramics structuring, may be used.

The combined imaging detector can be used for x-ray and gamma planar imaging. 3D-gamma imaging using statistical reconstruction (typically MLEM based) is possible in oncology when multiple gamma images from different pinholes overlap. This is comparable to the image information available in x-ray tomosynthesis. Fully three-dimensional tomographic images, CT from the x-ray detector and SPECT from the gamma detector, may be obtained by a 180°-sweep of the C-arm.

The combined imaging detector and imaging system may be applied in image-guided therapy, oncological intervention, SIRT (TARE), brachytherapy, RSO, tumor resection, biopsies, tumor thermal ablation, surgical oncology, percutaneous interventions, and vascular perfusion.

Figure 7:
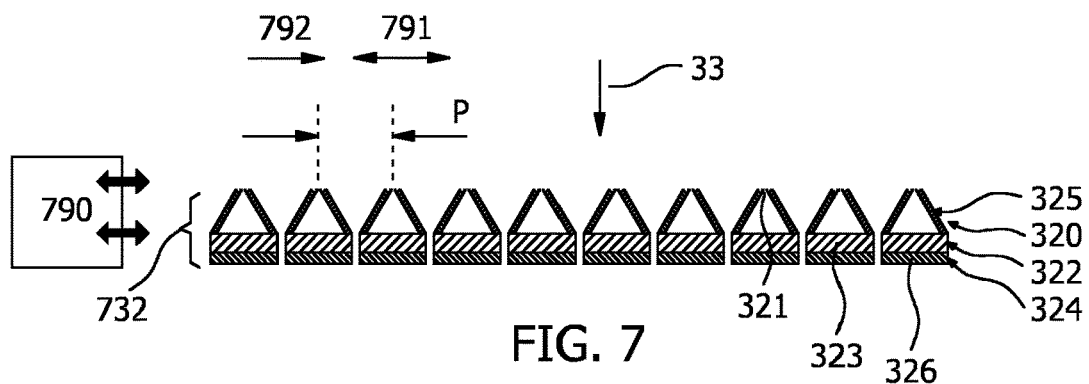
FIG. 7 illustrates an embodiment of a gamma detector 732 that includes an actuator 790.

FIG. 7 illustrates an embodiment of a gamma detector 732 that includes an actuator 790. Like-numbered items in FIG. 7 correspond to those that are also described in relation to FIG. 2. The gamma detector in FIG. 7 may be used in the absence of, or in combination with the disclosed X-ray detector 31, 41, e.g. in place of gamma detector 32 in FIG. 2. Returning to FIG. 7, in gamma detector 732, gamma collimator plate 320 that includes plurality of pinholes 321; and gamma conversion layer 322, 324, are arranged in a stacked configuration along radiation-receiving direction 33. Moreover, actuator 790 is configured to provide either i) a relative displacement between gamma collimator plate 320 and gamma conversion layer 322, 324; or ii) a displacement of gamma detector 732, in a displacement direction 791 that is perpendicular to the radiation-receiving direction 33. Actuator 790 may for example be a mechanical, hydraulic or piezoelectric actuator. In a preferred example a mechanical worm drive actuator is used. The effect of the displacement is that the field of view of each of the pinholes changes. In a preferred example pinholes 321 of gamma collimator plate 320 have a first pitch P in a first direction 792. First direction 792 is parallel to displacement direction 791. Moreover, preferably the displacement has a magnitude that is less than or equal to the first pitch P. Displacement direction 791 is illustrated in FIG. 7 as being in the direction of pitch P, however it is also to be appreciated that this displacement and the pitch may alternatively be directed towards or away from the plane of the drawing.

It has been realized that by displacing the gamma detector as described above, the field of view of each pinhole is adjusted so as to increase the overlap with the field of view of its un-displaced neighbouring pinhole. In so doing, sufficient gamma detection signals may be generated by the gamma detector 732 to reconstruct a tomographic, i.e. SPECT gamma image, rather than a scintigraphy image. This is the case particularly for relatively proximal imaged objects. In more detail, the reconstruction of a tomographic gamma image of an object requires gamma detection signals from at least two different viewing directions of the object. Each pinhole in plurality of pinholes 321 in gamma collimator plate 320 operates with its associated gamma conversion layer 322, 324 to provide gamma detection signals from a corresponding field of view, or viewing direction. For relatively distant pinhole-object distances the fields of view of neighbouring pinholes substantially overlap, whereas for relatively proximal pinhole-object distances the overlap between the fields of view of neighbouring pinholes is significantly less. Consequently for relatively distant pinhole-object distances there is typically sufficient data from adjacent pinholes to provide the at least two different viewing directions of the object required for tomographic image reconstruction. By contrast for relatively proximal pinhole-object distances there is typically only sufficient data for one viewing direction, or even no data at all for limited area between pinholes in a narrow region near the pinhole plate. By displacing the gamma detector as described above, the field of view of each pinhole is adjusted so as to provide at least sufficient data for a second viewing direction, particularly for relatively proximal pinhole-object distances. Sufficient data is thereby provided to reconstruct a tomographic, i.e. SPECT, image. Known image reconstruction techniques such as statistical reconstruction methods including Maximum Likelihood Estimation Method, i.e. MLEM, can be used for the reconstruction.

The magnitude of the displacement that is required to provide sufficient data for a second viewing angle depends primarily on the pinhole pitch, P, and the pinhole-object distance. A displacement that is equal to the pinhole pitch, P, provides complete data for two fields of view for a zero pinhole-object distance. For practical pinhole-object distances that are contemplated, sufficient data may be provided by a displacement that is equal to a fraction of the pinhole pitch, P. A displacement that exceeds the pinhole pitch, P, may be used to provide over-sampled, or redundant data.

Moreover, as described above, the displacement may be effected either as i) a relative displacement between the gamma collimator plate 320 and the gamma conversion layer 322, 324; or ii) a displacement of the gamma detector, in a displacement direction 791 that is perpendicular to the radiation-receiving direction 33. In a non-limiting example the pinhole pitch may for example be in the order of a few millimetres. Consequently the displacement may be provided by numerous actuators, such as for example a mechanical worm drive.

Figure 8:
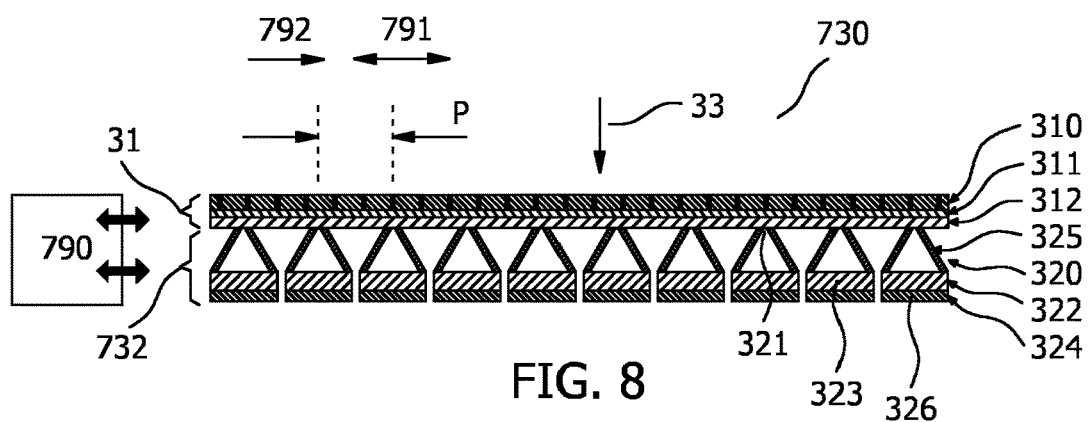
FIG. 8 illustrates an embodiment of a combined imaging detector 730 that includes gamma detector 732, an actuator 790 and an X-ray detector 31.

Clearly the same effect may also be achieved by displacing gamma detector 732 in the same manner when gamma detector 732 is combined with an X-ray detector in combined imaging detector 3, 30, 50, 60, 70, 100, 110 illustrated in FIGS. 1-6. Thereto, FIG. 8 illustrates an embodiment of a combined imaging detector 730 that includes gamma detector 732, an actuator 790 and an X-ray detector 31. X-ray detector 31 may operate in the same manner as described elsewhere herein.

In another embodiment a gamma imaging method is disclosed. The gamma imaging method may be used with gamma detector 732 and includes the steps of:
  generating gamma detection signals with the gamma detector 732 with the gamma collimator plate 320 and the gamma conversion layer 322, 324 in a first mutual arrangement;
  causing the actuator 790 to provide the relative displacement between the gamma collimator plate 320 and the gamma conversion layer 322, 324 such that the gamma collimator plate 320 and the gamma conversion layer 322, 324 are in a second mutual arrangement;
  generating gamma detection signals with the gamma detector 732 with the gamma collimator plate 320 and the gamma conversion layer 322, 324 in the second mutual arrangement; and
  reconstructing a gamma image based on the gamma detection signals generated with the gamma collimator plate 320 and the gamma conversion layer 322, 324 in the first mutual arrangement and the second mutual arrangement.

In a corresponding embodiment an imaging method is disclosed for use with the combined imaging detector 32. The imaging method includes the steps of:
  generating gamma detection signals with the gamma detector 32 with the combined imaging detector in a first position;
  translating the combined imaging detector perpendicularly with respect to the radiation receiving direction 33 to a second position;
  generating gamma detection signals with the gamma detector 32 with the combined detector in the second position; and
  reconstructing a gamma image based on the gamma detection signals generated with the combined imaging detector in the first position and in the second position.

Moreover, either of the above methods, optionally incorporating any other method steps disclosed herein, may be included as instructions in a computer program product which, when executed on a processor controlling the gamma detector 32, 732 according to claim 1, cause the processor to carry out said method steps. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk read only memory "CD-ROM", compact disk read/write "CD-R/W", Blu-Ray™ and DVD.

Figure 9:
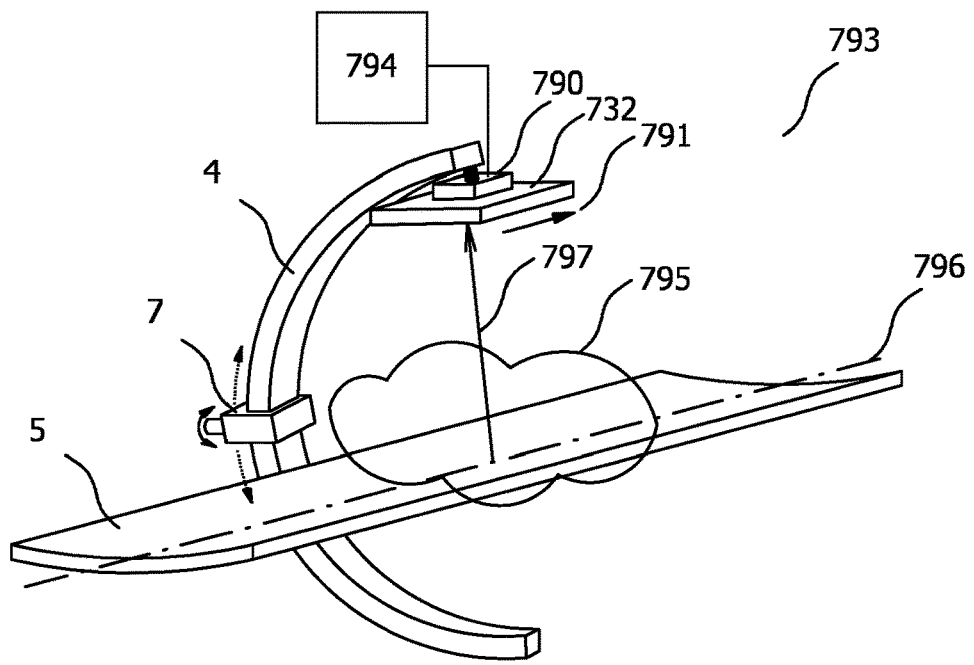
FIG. 9 illustrates a gamma imaging system 793 that includes gamma detector 732 and an actuator control system 794.

In another embodiment, FIG. 9 illustrates a gamma imaging system 793 that includes gamma detector 732 and an actuator control system 794. Gamma imaging system 793 has an imaging region 795 and an imaging axis 796 passing therethrough for receiving a patient along the imaging axis 796. The patient may be supported by patient table 5 that is configured to move parallel to imaging axis 796. Gamma detector 732 is disposed along a radius 797, i.e. radially, with respect to the imaging axis 796, and displacement direction 791 is perpendicular to the radius 797. Actuator control system 794 is configured to control actuator 790 to cause either i) a relative displacement between the gamma collimator plate 320 and the gamma conversion layer 322, 324, or ii) a displacement of the gamma detector 732 such that the gamma detector 732 generates gamma detection signals in each of two displacement positions for use in reconstructing a gamma image. Actuator control system 794 may for example include a processor that provides said control of the actuator. Preferably displacement direction 791 is parallel to imaging axis 796, although alternatively displacement direction 791 may be perpendicular to imaging axis 796. Gamma imaging system 793 may include a C-arm 4 that supports gamma detector 732 or an alternative support or gantry. Gamma imaging system 793 may be operated such that actuator control system 794 displaces the gamma detector between two positions, gamma detection signals of a region of interest being generated in each of the two positions in order to reconstruct a tomographic image of the region of interest.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A gamma detector for generating gamma detection signals in response to detected gamma quanta, the gamma detector comprising:
   a gamma collimator plate comprising a plurality of pinholes, wherein the pinholes of the gamma collimator plate have a first pitch in a first direction;
   a gamma conversion layer adapted to convert detected gamma quanta into gamma detection signals, wherein the gamma collimator plate and the gamma conversion layer are in contact with each other, and are arranged in a stacked configuration along a radiation-receiving direction; and
   an actuator configured to provide a relative displacement between the gamma collimator plate and the gamma conversion layer, wherein the displacement has a magnitude that is less than or equal to the first pitch.

2. A gamma imaging method for use with the gamma detector according to claim 1, the gamma imaging method comprising:
   generating gamma detection signals with the gamma detector with the gamma collimator plate and the gamma conversion layer in a first mutual arrangement;
   causing the actuator to provide the displacement between the gamma collimator plate and the gamma conversion layer such that the gamma collimator plate and the gamma conversion layer are in a second mutual arrangement;
   generating gamma detection signals with the gamma detector with the gamma collimator plate and the gamma conversion layer in the second mutual arrangement; and
   reconstructing a gamma image based on the gamma detection signals generated with the gamma collimator plate and the gamma conversion layer in the first mutual arrangement and the second mutual arrangement.

3. A tangible, non-transitory computer readable medium that stores instructions which, when executed on a processor controlling the gamma detector, cause the processor to carry out the gamma imaging method according to claim 2.

4. A gamma imaging system comprising the gamma detector according to claim 1, and further comprising an actuator control system;
   wherein the gamma imaging system has an imaging region and an imaging axis passing therethrough for receiving a patient along the imaging axis;
   wherein the gamma detector is disposed along a radius with respect to the imaging axis;
   wherein the displacement direction is perpendicular to the radius; and
   wherein the actuator control system is configured to control the actuator to cause either i) a relative displacement between the gamma collimator plate and the gamma conversion layer, or ii) a displacement of the gamma detector such that the gamma detector generates gamma detection signals in each of two displacement positions for use in reconstructing a gamma image.

5. The gamma imaging system according to claim 4, wherein the displacement direction is parallel to the imaging axis.

6. A combined imaging detector for detection of gamma and x-ray quanta, the combined imaging detector comprising the gamma detector according to claim 1; and an x-ray detector for generating x-ray detection signals in response to detected x-ray quanta, wherein the x-ray detector is arranged in a stacked configuration with respect to the gamma detector along the radiation-receiving direction.

7. The gamma detector as claimed in claim 1,
wherein a number of pinholes of said gamma collimator plate is equal to or smaller than a number of gamma detector elements of the gamma conversion layer, wherein one pinhole and one or more corresponding gamma detector elements are arranged in a stacked configuration along the radiation-receiving direction and the pinhole is centered with respect to the one or more corresponding gamma detector elements.

8. The gamma detector as claimed in claim 1,
wherein said gamma collimator plate is made from a lead or tungsten plate, in which the plurality of pinholes are formed.

9. The gamma detector as claimed in claim 1,
wherein said gamma collimator plate is made from an absorption plate, in which a plurality of pinhole inserts including said pinholes are integrated.

10. The gamma detector as claimed in claim 1,
wherein said pinholes are knife-edge or tapered pinholes.

11. The gamma detector as claimed in claim 1,
wherein the plurality of pinholes each have a projection area having a round, square, or hexagonal shape.

12. The gamma detector as claimed in claim 1,
wherein projection areas of neighboring pinholes overlap or wherein projection areas of neighboring pinholes are separated by septa.

13. The gamma detector as claimed in claim 1,
wherein said gamma conversion layer includes a direct gamma conversion layer or an indirect gamma conversion layer.

14. A combined imaging detector for detection of gamma quanta and x-ray quanta, the combined imaging detector comprising:
an x-ray detector adapted to generate x-ray detection signals in response to detected x-ray quanta, the x-ray detector comprising: an x-ray conversion layer adapted to convert detected x-ray quanta into x-ray detection signals; read-out electronics; and a foil substrate, the x-ray conversion layer and the read-out electronics being arranged on the foil substrate such that the read-out electronics are disposed laterally with respect to the x-ray conversion layer; and
a gamma detector adapted to generate gamma detection signals in response to detected gamma quanta, the gamma detector comprising: a gamma collimator plate comprising a plurality of pinholes, wherein material of the x-ray conversion layer adjacent to one or more of the plurality of pinholes is removed, or is thinner than in other areas not adjacent to the pinhole; and a gamma conversion layer adapted to convert detected gamma quanta into gamma detection signals, wherein the x-ray detector and the gamma detector are arranged in a stacked configuration along a radiation-receiving direction.

15. The combined imaging detector as claimed in claim 14,
wherein the gamma detector is controlled to generate gamma detection signals when no x-ray quanta are incident on the combined imaging detector.

16. The combined imaging detector as claimed in claim 14,
wherein said x-ray detector further comprises
an x-ray anti-scatter grid.

17. An imaging system comprising:
an x-ray source adapted to emit pulsed x-ray radiation comprising two split x-ray beams at different angles, and
a combined imaging detector adapted to detect gamma and x-ray quanta, the combined imaging detector comprising:
an x-ray detector adapted to generate x-ray detection signals in response to detected x-ray quanta; and
a gamma detector adapted to detect gamma detection signals in response to detected gamma quanta, the gamma detector comprising: a gamma collimator plate comprising a plurality of pinholes; and
a gamma conversion layer for converting detected gamma quanta into gamma detection signals, wherein the x-ray detector and the gamma detector are arranged in a stacked configuration along a radiation-receiving direction..

18. The imaging system as claimed in claim 17, further comprising a control unit configured to control said combined imaging detector to detect gamma quanta during intervals between x-ray pulses.

19. The imaging system as claimed in claim 18, wherein the control unit is further configured to either i) identify gamma detection signals generated by the gamma detector during x-ray pulses for exclusion from a reconstruction of a corresponding gamma image or ii) control the gamma detector to inhibit or suppress the generation of gamma detection signals during said x-ray pulses.

20. The imaging system as claimed in claim 18, wherein the control unit is configured to control the gamma detector to generate gamma detection signals only during intervals between x-ray pulses.

21. An imaging method for use with the combined imaging detector according to claim 14, the imaging method comprising:
generating gamma detection signals with the gamma detector with the combined imaging detector in a first position;
translating the combined imaging detector perpendicularly with respect to the radiation receiving direction to a second position;
generating gamma detection signals with the gamma detector with the combined detector in the second position; and
reconstructing a gamma image based on the gamma detection signals generated with the combined imaging detector in the first position and in the second position.

22. The imaging method as claimed in claim 21, wherein the pinholes of the gamma collimator plate have a first pitch in a first direction;
wherein the first direction is parallel to the direction of the translation; and
wherein the translation has a magnitude that is less than or equal to the first pitch .

23. A tangible non-transitory computer readable medium that stores instructions which, when executed on a processor controlling the gamma detector cause the processor to carry out the imaging method according to claim 22.

\* \* \* \* \*